United States Patent [19]

Hoegnelid

[11] Patent Number: 5,050,599
[45] Date of Patent: Sep. 24, 1991

[54] IMPLANTABLE MEDICAL DEVICE FOR DETECTING EVENTS OCCURRING WITH RESPECT TO A PHYSIOLOGICAL FUNCTION WITH VARIABLE SENSITIVITY AND A METHOD FOR THE OPERATION OF SUCH A DEVICE

[75] Inventor: Kurt Hoegnelid, Västerhaninge, Sweden

[73] Assignee: Siemens Aktiengesellschaft, Munich, Fed. Rep. of Germany

[21] Appl. No.: 525,133

[22] Filed: May 17, 1990

[30] Foreign Application Priority Data

May 22, 1989 [EP] European Pat. Off. ........ 89109157.1

[51] Int. Cl.⁵ ............................................ A61N 1/362
[52] U.S. Cl. ............................................ 128/419.0 PG
[58] Field of Search ................................ 128/419 PG

[56] References Cited

U.S. PATENT DOCUMENTS 4,552,154 11/1985 Hartlaub ............................. 128/702
4,766,902 8/1988 Schroeppel ................... 128/419 PG
4,768,511 9/1988 DeCote, Jr. ................... 128/419 PG
4,773,401 9/1988 Citak et al. .................... 128/419 PG

FOREIGN PATENT DOCUMENTS 0220916 5/1987 European Pat. Off. .

Primary Examiner—William E. Kamm
Assistant Examiner—Scott M. Getzow
Attorney, Agent, or Firm—Hill, Van Santen, Steadman & Simpson

[57] ABSTRACT

An implantable medical device comprising a first and a second detector means for detecting events corresponding to a physiological function of a living being and setting means for setting the sensitivity of the first detector means, the setting means automatically setting the sensitivity of the first detector means such that the first detector means detects every event detected by the second detector means.

18 Claims, 4 Drawing Sheets

IMPLANTABLE MEDICAL DEVICE FOR DETECTING EVENTS OCCURRING WITH RESPECT TO A PHYSIOLOGICAL FUNCTION WITH VARIABLE SENSITIVITY AND A METHOD FOR THE OPERATION OF SUCH A DEVICE

BACKGROUND OF THE INVENTION

The invention is directed to medical devices implantable into the body of a living being having detector means with variable sensitivity for detecting events occurring with respect to a physiological function. The invention is also directed to a method for the operation of such a device.

The term "sensitivity" as used herein is to be understood as a threshold that a signal parameter or signal parameters of a signal corresponding to the physiological function that is detected, for example the amplitude and/or the steepness of an electrical signal, must exceed in order to lead to a detection. A high sensitivity therefor corresponds to a low threshold, whereas a low sensitivity corresponds to a high threshold.

The term "stimulation intensity" is used comprehensively herein and includes, singly or in combination, the duration, frequency, repetition rate, amplitude, etc., with which means for stimulating are activated.

One problem that arises in prior art devices to which the invention relates is that while one would like to set the sensitivity optimally high in order to guarantee that all occurring events are in fact detected, on the other hand, the sensitivity cannot be set too high without risking that the detector means erroneously detects noises superimposed on the signal corresponding to the physiological function as events. In practice, the sensitivity is therefore usually set to a value that represents a compromise.

A device of the type initially described that is fashioned as a heart pacemaker is disclosed in the publication "Pulse Generator 704—Physician's Manual", produced by Siemens-Elema AB, Solna, Sweden. The publication is dated March 1985.

The disclosed heart pacemaker provides what is referred to as an intracardial electrocardiogram (IEKG) signal that is supplied to the detector means of the heart pacemaker. The IEKG signal is displayed in conjunction with registration means.

When a corresponding function of the heart pacemaker is activated, those events that the detector means of the heart pacemaker detects as natural heartbeats are marked in a registration of this signal. An attending physician is thus in a position to initially set the detector means to a sensitivity at which all events in the registered signal, that the physician recognizes as natural heartbeats, are detected.

Subsequently, the attending physician sets the sensitivity of the detector means to a value that is higher by a safety margin, this value being selected depending on the individual conditions of the patient. Since, after the end of a stay in a clinic in connection with the implantation of a pacemaker, the patient only sees the attending physician at great intervals, there is the risk that conditions can arise that no longer correspond to the adjustment of the sensitivity of the detector means that was selected by the attending physician. For example, the position of the endocardial electrode that conducts signals corresponding to the electrical activity of the heart to the detector means can change. This can lead to malfunctions, regardless of whether the existing adjustment of the sensitivity is too high or low for the altered conditions. In the former case, there is the risk that noise signals will be erroneously detected as natural heartbeats and, consequently, a stimulation of the heart that is required per se is omitted. In the latter case, there is the risk that all natural heartbeats that occur will not be detected and, consequently, the heart of the patient will be unnecessarily stimulated. This is just as undesirable since the well-being of the patient will be jeopardized.

SUMMARY OF THE INVENTION

The invention provides an implantable device of the type discussed above wherein the detector means always operates with the required sensitivity without interaction on the part of the attending physician. The invention also provides a method for the operation of the device that enables adaptation of the sensitivity of the detector means to changing conditions in a manner that is safe for the patient and that saves energy.

To this end, in an embodiment, the invention provides a medical device implantable into the body of a living being comprising a first detector means for the detection of events occurring with respect to a physiological function of the living being, setting means for setting the sensitivity (S) of the first detector means; and a second detector means for the detection of the events occurring with respect to the physiological function, the sensitivity thereof at least corresponding to the respectively set sensitivity (S) of the first detector means, whereby the setting means automatically sets the sensitivity (S) of the first detector means such that the first detector means detects the events detected by the second detector means.

In accordance therewith, the sensitivity of the first detector means, that represents the actual detector means with which the events occurring with respect to the physiological function are detected, is set on the basis of a second detector means provided only as a reference. It is thereby expedient that the second detector means (that preferably has a higher sensitivity than the respectively set sensitivity of the first detector means) works on a function principle that deviates from that of the first detector means, i.e. detects the events with respect to the physiological function on the basis of a different signal or at least detects events on the basis of a different signal parameter than that used by the first detector means. Since the sensitivities of the two detector means can potentially not be directly be compared to one another in terms of their numerical value under these conditions, what is to be understood here by identical sensitivity is that an event that can just still be detected with the first detector means can also be detected with the second detector means. A greater sensitivity of the second detector means then means that this still detects events that the first detector means is no longer capable of detecting.

In one embodiment, the sensitivity of the first detector means that is set higher by a safety margin selectable depending on the individual conditions existing in the patient and the minimum value of the sensitivity required for the detection of all events detected by the second detector means. A reliable operation of the device of the invention is thus guaranteed under all circumstances.

In a preferred embodiment of the invention, the device is a heart pacemaker. This embodiment has the advantage that the detection of an event with the second detector means ensues a few milliseconds after the detection of the same event with the first detector means. Since the detections do not appear simultaneously, it is easy to make a determination as to whether an event detected with the second detector means is also detected by the first detector means, since the only thing that must be checked is to see whether a detection by the first detector means also occurred briefly before the detection of an event by the second detector means. The electrode required for producing an electrical connection of the second detector means to the heart of the patient, moreover, can simultaneously serve to supply the signal corresponding to the electrical activity of the heart to the first detector means.

In another embodiment, the signal corresponding to the impedance of the heart is acquired on the basis of an exclusive alternating current measurement. Disturbing influences for example, such as can appear in the tissue of the heart muscle as a potential briefly after a stimulation pulse that deviates from its quiescent potential, are avoided. When the measurement ensues with an alternating current that has an extremely high frequency, for example several Kilohertz, disturbances of the first detector means are impossible since this detector means does not respond to such high frequencies.

In another embodiment, the invention provides a method for operating a device such as those described above. In accordance therewith, the automatic setting of the sensitivity does not occur continuously but only between successive time intervals that have a duration on the order of magnitude of hours. The second detector means, thus, has to be placed in operation only at greater time intervals, this reducing energy consumption of the device and, thus, on the useful life of a battery that supplies the device. Since continuous changes in the sensitivity of the first detector means are usually not required, no adverse consequences for the patient need be feared due to the described, intermittent operation.

In case of potential disturbances, however, in another embodiment, the invention provides that a correction of the sensitivity of the first detector circuit can quickly ensue since a check is carried out between intermediate intervals having a duration on the order of magnitude of minutes. These checks are carried out to see whether the sensitivity of the first detector means is set high enough in order to be able to detect events detected by the second detector means.

Another embodiment of the invention provides an advantage in that a sensitivity of the first detector means is set that is based on the minimum value of the sensitivity of the first detector means at which the first detector means detects every event detected by the second detector means. What is thereby assured is that the sensitivity of the first detector means is not higher than absolutely necessary, taking safety margins into consideration. It is thus assured that, first, misdetections are avoided and, second, all events are detected by the first detector means.

Another embodiment of the invention is directed to the calculation of the minimum value of the sensitivity of the first detector means. In case of an increase in the minimum value of the sensitivity, it is thereby assured that the higher minimum value of the sensitivity can be quickly found, so that the number of events that cannot be detected by the first detector means is limited to a minimum. In case of a reduction in the minimum value of the sensitivity, the lower minimum value is calculated step-by-step between the longer intervals given greater changes. This offers the advantage that, given only brief-duration changes of the minimum value of the sensitivity, the sensitivity of the first detector means is not lowered to such an extent that there is the risk that events cannot be detected.

Another embodiment of the invention provides an advantage in that at least one of two successive events during the automatic adjustment of the sensitivity of the first detector means is detected, so that an adequate stimulation of the physiological function is also assured during the automatic setting of the sensitivity of the first detector means.

DETAILED DESCRIPTION OF THE PRESENTLY PREFERRED EMBODIMENTS

Figure 1:
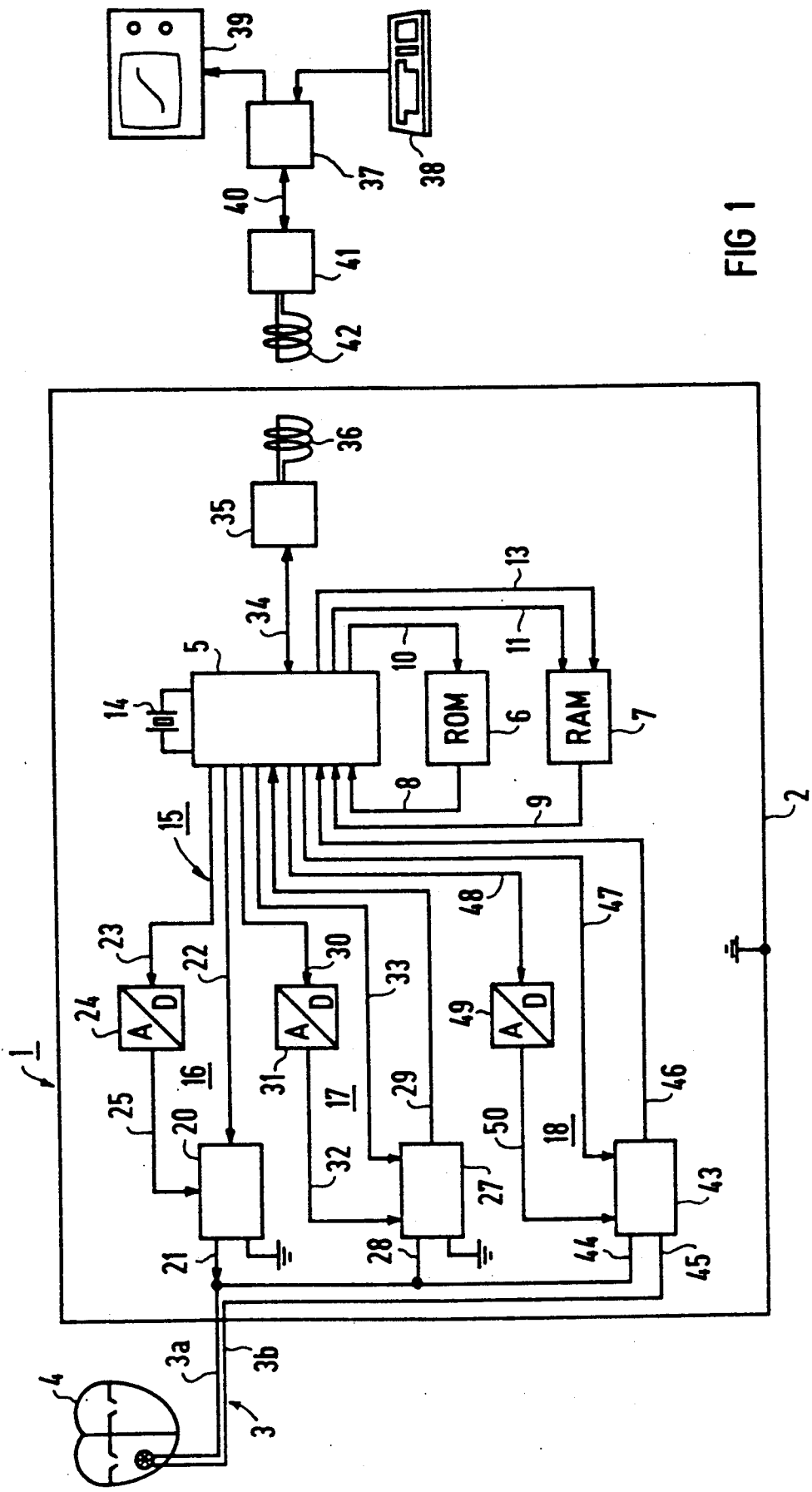
FIG. 1 is a block diagram of a heart pacemaker embodying principles of the invention.

In FIG. 1, there is illustrated in block diagram form a heart pacemaker 1 embodying principles of the invention. The component parts of the heart pacemaker 1 are housed in a schematically indicated, hermetically tight housing comprising an electrically conductive material, for example titanium.

The pacemaker 1 preferably is operated in the VVI mode. A bipolar electrode 3 leads from the heart pacemaker 1 to a schematically indicated heart 4 of a living being and is implanted there in a ventricle, preferably the right ventricle. The bipolar electrode 3 has two lines 3a, 3b.

Among other things, the heart pacemaker 1 comprises a microprocessor 5 to which a read-only memory (ROM) 6, and a random access write-read memory (RAM) 7 are allocated. The ROM 6 and RAM 7 are in communication with the microprocessor 5 via data lines 8 and 9 and address lines 10 and 11. A line 13 that serves the purpose of switching the RAM 7 from write mode to read mode and vice versa also leads from the microprocessor 5 to the RAM 7.

A program with which all functions of the heart pacemaker 1 are controlled is stored in the ROM 6. When, thus, it is mentioned below that the microprocessor 5 executes a specific function, what is to be thereby understood is that the microprocessor 5 is activated for executing the specific function by virtue of executing the program stored in the ROM 6 in view of data stored in the RAM 7 and data supplied to the microprocessor 5 in some other fashion, for example, via input wiring. When it is mentioned that the microprocessor 5 sets a defined value for a parameter, then this usually means—if not otherwise specified—that data corresponding to the defined value are stored in the RAM 7 and that the microprocessor 5 can access these data.

With continued reference to FIG. 1, it is illustrated that a crystal 14 is connected to the microprocessor 5. As is conventional, this crystal 14 serves the purpose of generating the clock signals required for the operation of the microprocessor 5 and also representing the time reference for the operation of the heart pacemaker 1.

The microprocessor 5 has an input/output wiring 15 that comprises a plurality of channels 16, 17 and 18. These channels are described below.

The channel 16 serves to supply the heart with stimulation pulses, as needed. The channel 16 therefore includes a stimulation pulse generator 20 that comprises a signal output connected via an output line 21 to the line 3a of the electrode 3 and a terminal that carries a reference potential. The terminal carrying the reference potential is electrically connected to the housing 2. This is illustrated in that both the terminal of the stimulation pulse generator 20 carrying the reference potential as well as the housing 2 are provided with a ground symbol.

Although a bipolar electrode 3 is present, the stimulation ensues unipolarly. The stimulation pulse generator 20 can be activated to output a stimulation pulse via a line 22 that is connected to a corresponding output of the microprocessor 5. Digital data that relate to the duration and to the amplitude and, thus, to the energy content of the stimulation pulses proceed from the microprocessor 5 via a line 23 to a digital-to-analog interface 24 that supplies the stimulation pulse generator 20 with analog control signals via a control line 25, these analog control signals corresponding to the digital data. These analog control signals set the stimulation pulse generator 20 so that it generates stimulation pulses having a defined energy content, as needed, and thus so that it stimulates the heart 4 of the living being with a defined stimulation intensity.

The channel 17 has a first detector means 27 that exclusively serves the purpose of detecting natural heartbeats. The first detector means 27 has a signal input connected via an input line 28 to the line 3a of the electrode 3 and has a terminal that carries a reference potential. As becomes clear in view of the ground symbol, the reference potential of the detector means 27 is the same as that of the corresponding of the stimulation pulse generator 20 and the housing 2.

Although a bipolar electrode 3 is present, the detection of natural heartbeats with the first detector means 27 ensues unipolarly. When the second detector means 43 detects a natural heartbeat in the signal corresponding to the electrical activity of the heart 4 that is supplied to it via the line 3a of the electrode 3, it forwards a signal indicating this detection via a line 29 to a corresponding input of the microprocessor 5. The first detector means 27 outputs this signal when an event having a steepness and/or amplitude typical of a natural heartbeat appears in the signal corresponding to the electrical activity of the heart 4.

The microprocessor 5 is connected via a line 30 to a digital-to-analog interface 31 that forwards the digital data supplied to it from the microprocessor 5 to the first detector means 27 via a control line 32 as corresponding analog signals. The digital data or, respectively, the corresponding analog signals serve to set the sensitivity of the first detector means 27, i.e. that steepness and/or amplitude that an event in the signal corresponding to the electrical activity of the heart 4 must minimally exhibit in order to be detected as a natural heartbeat. Additionally, the microprocessors can supply a signal to the first detector means 27 via control line 33 that completely inhibits this first detector means 27, so that no signals indicating the detection of a natural heartbeat can proceed to the microprocessor 5.

When the microprocessor 5 receives a signal that corresponds to the detection of a natural heartbeat with the first detector means 27 via the line 29, or when the microprocessor 5 activates the stimulation pulse generator 20 via the line 22 to output a stimulation pulse, the microprocessor 5 begins to work as a counter and begins to count off a plurality of clock pulses derived from the oscillation of the crystal 14, this plurality of clock pulses corresponding to a base time interval. The base time interval defines that stimulation frequency with which the heart 4 is stimulated given the absence of natural heartbeats. When no signal indicating the detection of a natural heartbeat is supplied to the microprocessor 5 via the channel 17 during the base time interval, the microprocessor 5 activates the stimulation pulse generator 20 via the line 22 after the expiration of the base time interval. Following the output of a stimulation pulse, the microprocessor 5 again begins to count off a plurality of clock pulses that corresponds to the base time interval that defines the stimulation frequency. When, by contrast, the microprocessor 5 receives a signal from the first detector means 27 that indicates the detection of a natural heartbeat during the course of the base time interval, it aborts the described counting process as long as a further time interval, referred to as the refractory time, has expired and starts the described counting process again without outputting a stimulation pulse. The detection of a natural heartbeat with the first detector means 27 thus inhibits the output of a stimulation pulse.

The refractory time is fundamentally shorter than the base time interval (programmable, for example, to values between 400 and 2000 milliseconds) and lasts between about 250 and 450 milliseconds. The refractory time also is programmable and is divided into an absolute refractory time usually having a duration of 125 milliseconds and into a relative refractory time corresponding to the remaining time of the refractory time. The refractory time begins to run simultaneously with the base time interval and is calculated by the microprocessor 5 during the course of the same counting process that also serves the purpose of calculating the base time interval.

During the absolute refractory time, the first detector means 27 in the channel 17 is inhibited, this being achieved because the microprocessor 5 supplies the first detector means 27 with an appropriate signal via the control line 33. As a consequence of the inhibition of the first detector means 27, the first detector means 27 is absolutely inca-able of detecting heartbeats during the duration of the absolute refractory time, i.e. corresponding signals cannot proceed to the microprocessor 5.

After the expiration of the absolute refractory time, the microprocessor 5 reactivates the first detector means 27, so that this is able to detect natural heartbeats. When, in contrast to a detection of a heartbeat after the expiration of the refractory time, a heartbeat is detected during the relative refractory time, the microprocessor 5 does not abort the counting process for calculating the base time interval but continues it and ends it with an activation of the stimulation pulse generator 20. After the detection of a natural heartbeat, however, the microprocessor 5 again starts the full refractory time.

What is thereby achieved is that stimulation pulses are generated with a stimulation frequency defined by the programmed base time interval independently of the appearance of natural heartbeats. Even when the spontaneous heartbeat frequency is so high that natural heartbeats always appear within the relative refractory time, stimulation pulses are output with the stimulation frequency defined by the programmed base time interval, namely until the spontaneous heartbeat frequency has fallen below a frequency whose period duration corresponds to the respectively set refractory time. This function makes it possible to end certain re-entry tachycardia.

The microprocessor 5 is also connected via a line 34 to a telemetry circuit 35 to which a transmission/reception coil 36 is connected. The heart pacemaker 1 is thus able to exchange data with an external programming device 37 having a keyboard 38 and a monitor 39, since the programming device 37 is connected via a line 40 to a second telemetry circuit 41 to which a transmission/-reception coil 42 is connected. For the exchange of data between the heart pacemaker 1 and the programming device 37, the transmission/reception coil 42 of the telemetry circuit 41 belonging to the programming device 37 is positioned such on the body surface of the living being wearing the heart pacemaker 1 so that it is inductively coupled with the transmission/reception coil 36 of the heart pacemaker 1. It is then possible to supply the data situated in the ROM 6 and in the RAM 7 to the programming device 37 for checking. Moreover, there is the possibility of supplying the RAM 7 of the heart pacemaker 1 with modified or, respectively, additional data from the programming device 37, these modified or additional data influencing and modifying the operating behavior of the heart pacemaker 1, i.e. its interaction with the heart 4. This procedure is generally referred to as programming.

The channel 18 of the input/output wiring 15 of the microprocessor 5 serves to make data available to the microprocessor 5 that, with reference to the program stored in the ROM 6, allow the microprocessor, first, to set the stimulation intensity, i.e. the energy content of the stimulation pulses generated with the stimulation pulse generator 20 such that a stimulation pulse also in fact triggers a stimulated heartbeat and, second, to set the sensitivity of the first detector means 27 such that a disturbance-free and reliable detection of all natural heartbeats is guaranteed. To this end, the channel 18 contains a second detector means 43 that is provided both for the detection of natural as well as stimulated heartbeats. The second detector means 43 has two terminals one of which is connected via the line 44 to the line 3a and the other is connected via a line 45 to the line 3b of the bipolar electrode 3.

In contrast to the first detector means 27, the second detector means 43 detects natural heartbeats as well as stimulated heartbeats, i.e. heartbeats that appear in response to a stimulation pulse output by the stimulation pulse generator 20. When the second detector means 43 detects a stimulated or a natural, i.e. spontaneously occurring, heartbeat. An appropriate signal is supplied via the line 46 from the output of the second detector means 43 to a corresponding input of the microprocessor 5. Then, at that time, the microprocessor 5 will be able to inhibit the output of the second detector means 43, by generating an appropriate signal via a control line 47.

The sensitivity of the second detector means 43 can be set by the microprocessor 5 by supplying digital data via the line 48 to a digital-to-analog interface 49 which, in turn, converts the digital data into a corresponding analog signal that is supplied to the second detector means 43 via a control line 50. In a way to be set forth in detail, the analog signal supplied via the line 50 defines the sensitivity of the second detector means 43, the microprocessor 5 normally setting this sensitivity equal to or higher than the sensitivity of the first detector means 27.

In contrast to the first detector means 27 whose output is enabled by the microprocessor 5 only after the expiration of the absolute refractory time, the second detector means 43 must be able to detect stimulated heartbeats during the absolute refractory time. The microprocessor 5 thus enables the output of the second detector means 43 not only after the expiration of a refractory time until the appearance of a natural heartbeat or until the output of a stimulation pulse, but for a few milliseconds after the output of a stimulation pulse, enabling it for a short time interval, for example, 100 milliseconds. What is critical, however, is that neither the detection of a stimulated heartbeat nor the detection of a natural heartbeat by the second detector means 43 can inhibit the output of a stimulation pulse. Such inhibition occurs only when a natural heartbeat is detected by the first detector means 27 under the conditions set forth above.

The automatic setting of the energy content of the stimulation pulses generated by the stimulation pulse generator 20 will now be described. The microprocessor 5—after the output of a stimulation pulse—checks to see whether a signal indicating the detection of a stimulated heartbeat arrives via the line 46 from the output of the second detector means 43, then enabled. If no heartbeat is detected, the microprocessor 5 increases the energy content of the next stimulation pulse by supplying digital data to the digital-to-analog interface 24 which in turn converts the digital data into an analog signal that sets the stimulation pulse generator 20 such that the stimulation pulse generator 20 outputs a stimulation pulse having increased energy content. This process continues until the second detector means 43 detects a stimulated heartbeat after a stimulation pulse. Via the digital-to-analog interface 24, the microprocessor 5 thereby sets the stimulation pulse generator 20 such that the energy content of the generated stimulation pulses corresponds to the sum of a minimum energy content (minimum value of the energy content) needed to stimulate a heartbeat that the second detector means 43 can still detect after the output of a stimulation pulse, and of a safety margin, for example 50% of the minimum energy content. The minimum energy content thereby corresponds to what is referred to as the stimulation threshold that the energy content of a stimulation pulse must at least reach in order to be able to trigger a stimulated heartbeat.

For calculating the minimum energy content, the microprocessor 5, commencing with a value at which the second detector means 43 detects a stimulated heartbeat after every stimulation pulse of a sequence of stimulation pulses, gradually lowers the energy content of the stimulation pulses until no stimulated heartbeat can be detected by the second detector means 43 following individual stimulation pulses. Proceeding on the basis of the value of the energy content found in this way, the microprocessor 5 again gradually increases the energy content of the stimulation pulses, namely to just such an extent until the second detector means 42 again detects a stimulated heartbeat after every stimulation pulse. The value found in this way represents the minimum energy content of the stimulation pulses.

What is achieved by the described setting of the energy content of the stimulation pulses is that, first, the safety of the patient is guaranteed since the stimulation always occurs with stimulation pulses whose energy content lies above the minimum energy content by a safety margin. Second, it is assured that the energy consumption of the device due to the output of stimulation pulses is not higher than necessary since the energy content of the stimulation pulses is always based on the required minimum energy content.

The automatic setting of the sensitivity of the first detector means 27 ensues such that, after the expiration of the absolute refractory time, the microprocessor 5 checks to see whether a natural heartbeat detected with the second detector means 43 was also detected with the first detector means 27. This is possible since the microprocessor 5 activates the first and the second detector means 27 and, respectively, 43 after the respective expiration of the absolute refractory time. When the detection of a natural heartbeat is detected only by the second detector means 43, the microprocessor 5 increases the sensitivity of the first detector means 27 in that it supplies digital data to the digital-to-analog interface 31 that the latter converts into an appropriate analog signal that set the sensitivity of the first detector means 27 such that its sensitivity is increased over the previously set value, this ensues until a setting for the sensitivity of the first detector means 27 has been found of which the first detector means 27 also detects the natural heartbeats detected by the second detector means 43.

It is understood that as a result, the sensitivity of the second detector means 43 must correspond at least to the sensitivity of the first detector means 27. However, the microprocessor 5 sets the sensitivity of the second detector means 43 noticeably higher than that of the first detector means 27. But, the sensitivity of the second detector means 43 cannot be arbitrarily increased since it must be assured that disturbances and noise do not lead to misdetections. The microprocessor 5 therefore sets the sensitivity of the first detector means 27 via the digital-to-analog interface 31 so that it is higher by a safety margin than a minimum sensitivity (minimum value of the sensitivity) at which the first detector means 27 still just detects a natural heartbeat also detected by the second detector means 43. For example, 50% of the minimum sensitivity comes into consideration as a safety margin.

For calculating the minimum sensitivity, the microprocessor 5—proceeding from a value at which the first detector means 27 detects every natural heartbeat detected by the second detector means 43—gradually lowers the sensitivity of the first detector means 27 until at least some natural heartbeats detected by the second detector means 43 can no longer be detected by the first detector means 27. Proceeding from the value of the sensitivity found in this way, the microprocessor 5 again gradually increases the sensitivity of the first detector means 27 until the first detector means 27 just detects every natural heartbeat detected by the second detector means 43. The value of the sensitivity of the first detector means 27 found in this way is the minimum sensitivity.

The described setting of the sensitivity of the first detector means 27 offers several advantages. First, it is guaranteed, in the interest of a patient, that within the sensitivity safety margin all natural heartbeats can in fact be detected by the first detector means 27. Second, it is assured as a consequence of the fact that the setting of the sensitivity ensues on the basis of the minimum sensitivity that the actual existing sensitivity is never higher than is absolutely required in the interest of the patient, so that the risk of misdetections is extremely low.

Figure 2:
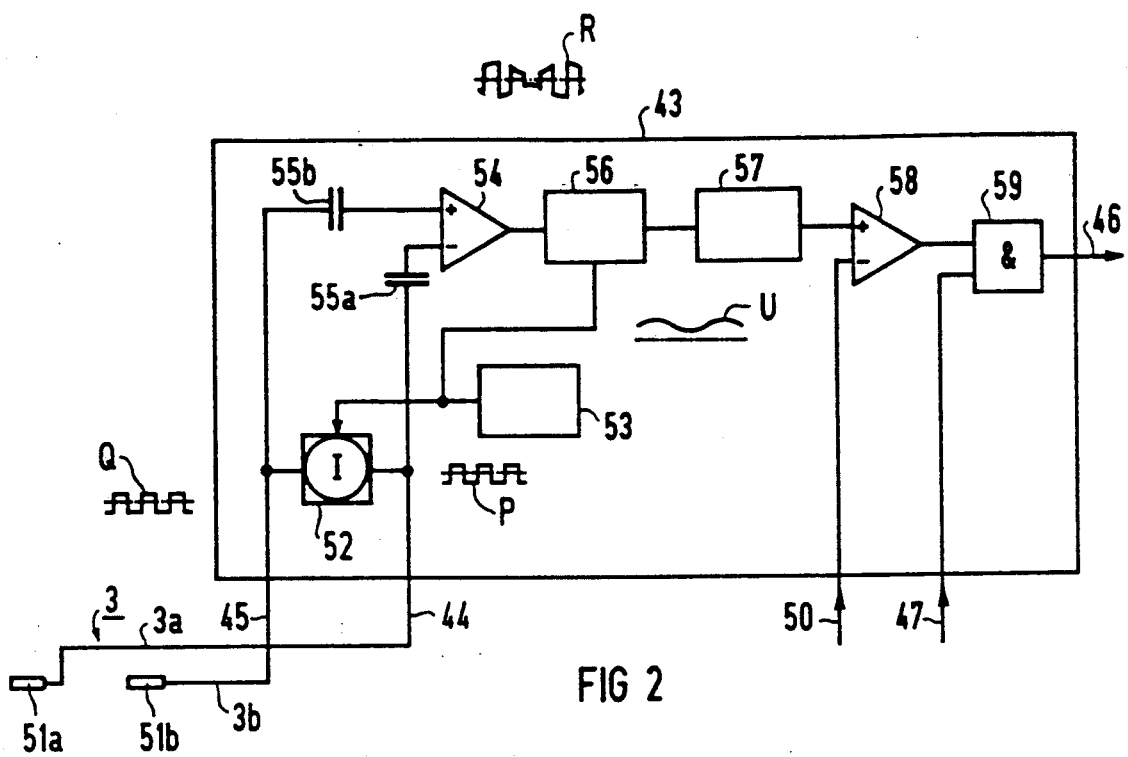
FIG. 2 is a block diagram of a second detector means of the heart pacemaker of FIG. 1.

An exemplary embodiment of the second detector means 43 is illustrated in FIG. 2. What is provided is a detector means that forms a signal that corresponds to the external impedance present between its terminals. What the term "external impedance" implies is that the input impedance of the second detector means 43 is not contained in the external impedance. What, so to speak, the external impedance involves is the source impedance that the second detector means 43 sees. This source impedance derives from the impedance of the bipolar electrode 3 schematically indicated in FIG. 2 with its lines 3a and 3b and from the impedance of the heart muscle tissue situated between the contact parts 51a and 51b that have an electrically conductive connection to the heart, given in implanted electrode.

The impedance of the heart muscle tissue changes, as a consequence of heart action, in harmony with the heart action. This can be understood from FIG. 3 wherein an electrical signal ES corresponding to the electrical activity of the heart for a plurality of natural heartbeats and a signal IS that corresponds to the electrical impedance of the heart are illustrated so that they can be compared.

As illustrated, the second detector means 43 comprises a bipolar, modulatable current source 52 that is connected parallel to the source impedance between the terminals of the second detector means 43. The current source 52 is connected to an oscillator 53 that generates a square-wave signal P with a constant amplitude and with a constant frequency that is noticeably higher than the anticipated heartbeat frequency. For example, 4 kHz can be the frequency of the square-wave signal.

The oscillator 53 modulates the current source 52 such that the latter generates an alternating current Q having a constant amplitude that corresponds to the signal of the oscillator 53 in terms of its frequency and curve shape and that is symmetrical relative to the zero line. This alternative current Q flows through the source impedance connected to the second detector means 43.

The voltage drop arising across the source impedance as a consequence of the alternating current Q is amplified by a differential amplifier 54 whose inputs are connected via coupling capacitors 55a and 55b to the lines 44 and 45, respectively. As a consequence of the coupling capacitors 55a, 55b, the differential amplifier 54 amplifies only the voltage drop produced by the alternating components of the current, this representing a measure of the existing source impedance. Since the impedance of the electrode 3 does not change, the change of the source impedance occurs exclusively because of impedance changes of the heart as a consequence of heart action. An output signal R of the differential amplifier 54 is also symmetrical about the zero line thus reflects the impedance curve of the heart and, thus, the heart action.

Figure 3:
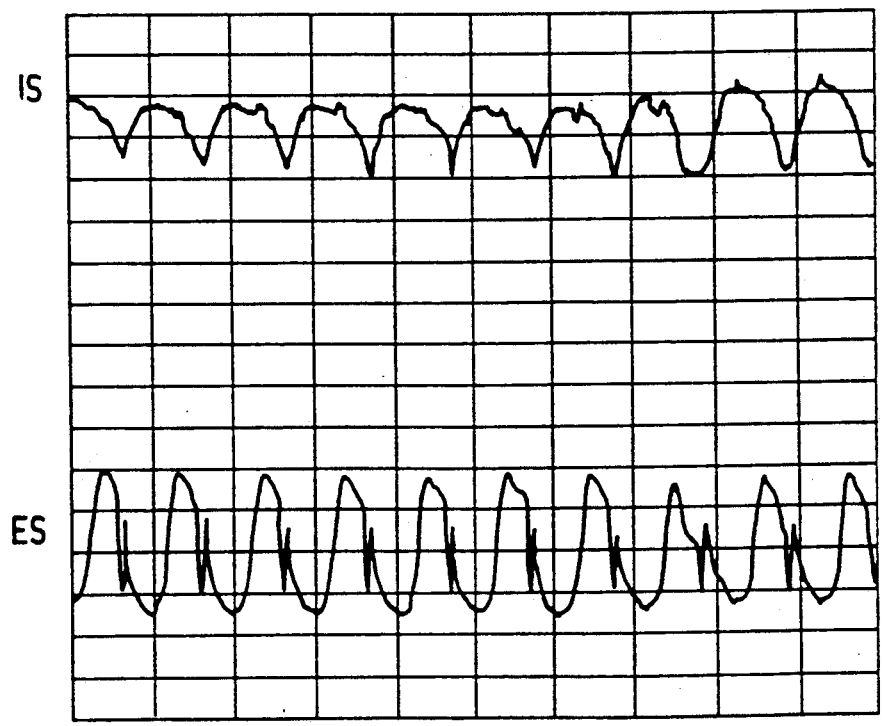
FIG. 3 is a graph illustrating a signal corresponding to electrical activity of a heart for a plurality of natural heartbeats as well as a signal corresponding to the impedance of the heart.

The output signal R of the differential amplifier 54 is supplied to a demodulator 56. The demodulator 56 demodulates the output signal R of the differential amplifier 54 as a consequence of the fact that the signal Q of the oscillator 53 is supplied to the demodulator 56 in correct phase relation to the modulation of the power source 52, so that a unipolar signal U, whose curve corresponds to the impedance curve of the heart or, respectively, of the heart action and that essentially corresponds to the signal IS of FIG. 3 is present at the output of the demodulator 56.

The unipolar signal U is supplied to a band-pass filter 57 whose transfer function is selected so that only those signal parts that are typical in terms of frequency or, respectively, steepness of heartbeats whether natural or stimulated can pass the band-pass filter 57.

The output signal of the band-pass filter 57 proceeds to the one input of a comparator 58 that compares the amplitude thereof to a threshold signal that is supplied to its other input via the control line 50. The threshold signal is the output signal of the digital-to-analog interface 49. When the amplitude of the output signal of the band-pass filter 57 exceeds the level of the threshold signal, the output signal of the comparator 58 changes from one extreme value to another extreme value. The original output signal of the comparator 58 is restored when the amplitude of the output signal of the band-pass filter 57 drops below the amplitude of the threshold signal.

In the illustrated embodiment, the output signal of the comparator 58 has the value logical "0" as long as the amplitude of the output signal of the band-pass filter 57 does not exceed the threshold signal. When a transgression of the threshold signal amplitude occurs, the output signal of the comparator 58 changes to a logical "1". When, thus, the microprocessor 5 sets the threshold signal via the digital-to-analog interface 49 so that it has an amplitude that exceeds the amplitude of the output signal of the band-pass filter 57, a signal that has the level logical "1" in the case of the detection of a heartbeat is available at the output of the comparator 58.

As further illustrated, the output signal of the comparator 58, however, is not directly supplied to the microprocessor 5 but proceeds to one input of an AND gate 59 whose output is connected to the line 46 leading to the microprocessor 5. The control line 47 is connected to another input of the AND gate 59. It thus becomes clear that the signals indicating the detection of a natural or stimulated heartbeat can only proceed via the line 46 to the microprocessor 5 when the latter enables the output of the second detector means 43 in that it supplies the AND gate 59 with a logical "1" signal via the control line 47.

Alternatively, there is also the possibility of switching the entire detector means 43 off during timespans wherein it is not required. This would lower the power consumption of the heart pacemaker because the entire detector means would use no current.

Further, the oscillator 53 need not necessarily be present as a separate circuit. The square-wave signal required for the modulation of the current source 52 and for the synchronization of the demodulator 56 can also be derived from the oscillation of the crystal 14 connected to the microprocessor 5.

In conjunction with the detection of stimulated heartbeats, the described fashioning of the second detector means 43 offers the advantage that the electrical signal corresponding to the impedance of the heart is exclusively calculated on the basis of that voltage drop across the source impedance that appears as a consequence of the alternating current output by the current source 52. This calculation arises as a result of the fact that the heart muscle tissue in the region of the contact 51a of the electrode 3 has a potential that deviates from the potential of the heart muscle tissue in the region of the contact 51b immediately after a stimulation pulse—and the detection of a stimulated heartbeat that must be ensue at this time cannot occur.

In conjunction with the automatic setting of the sensitivity of the first detector means 27, the described embodiment of the second detector means 43 offers the advantage that the detection of the same natural heartbeat with the first detector means 27 and with the second detector means 43 does not occurs simultaneously, which could lead to problems when processing the corresponding signals with the microprocessor 5. On the contrary, the detection with the second detector means 43 occur a short time after the corresponding detection with the first detector means 27. In conjunction with the automatic setting of the sensitivity of the first detector means 27, thus, the microprocessor 5 must merely check whether the detection of a natural heartbeat with the second detector means 43 is preceded by a corresponding detection with the first detector means 27. Malfunctions of the first detector means 27 due to the alternating current of the second detector means 43 need not be feared since the frequency of the alternating current is high enough so that the first detector means 27 cannot respond thereto.

Figure 4:
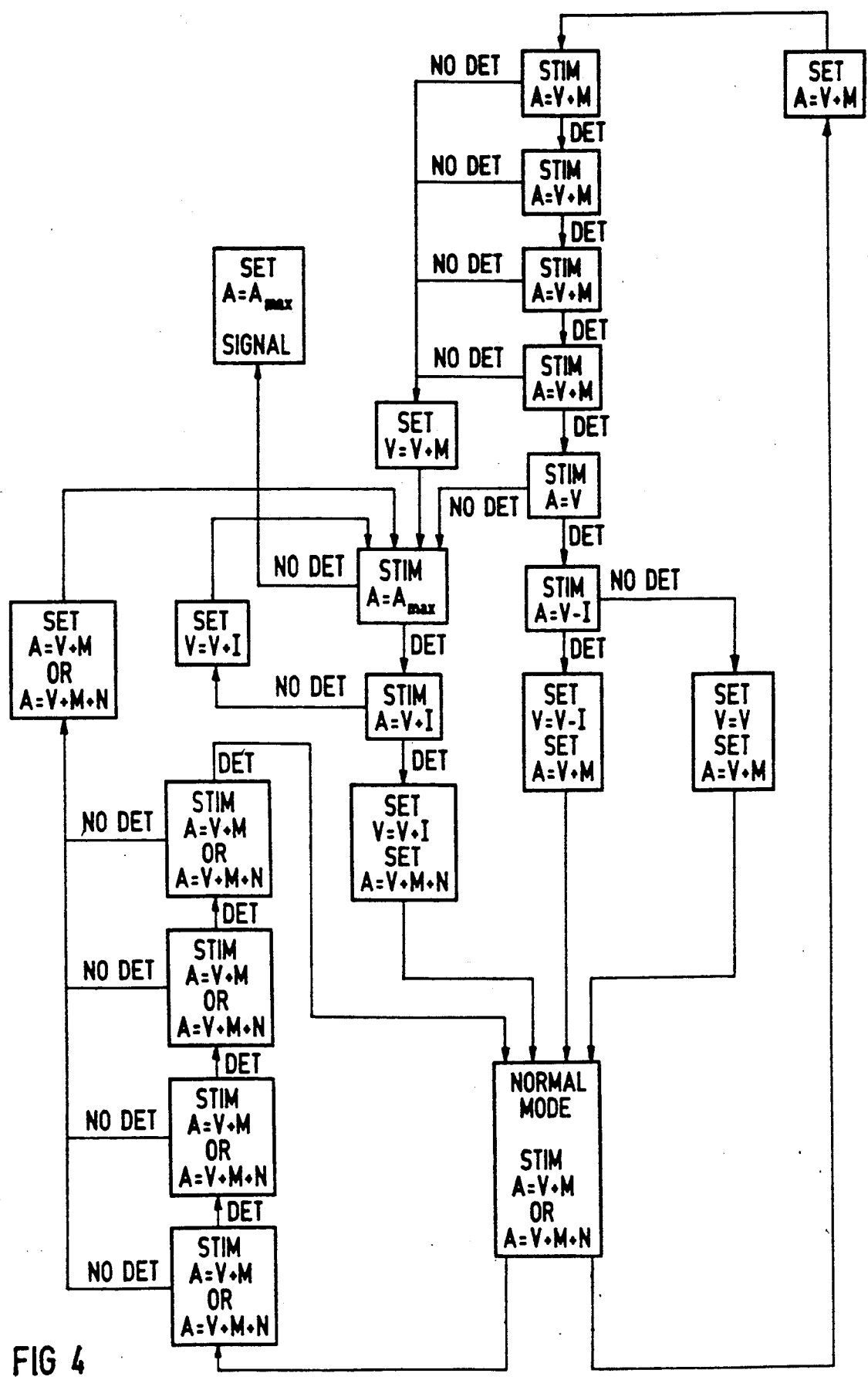
FIG. 4 is a flow chart that illustrates a method for automatically setting energy content of stimulation pulses of the heart pacemaker of FIG. 1.
Figure 5:
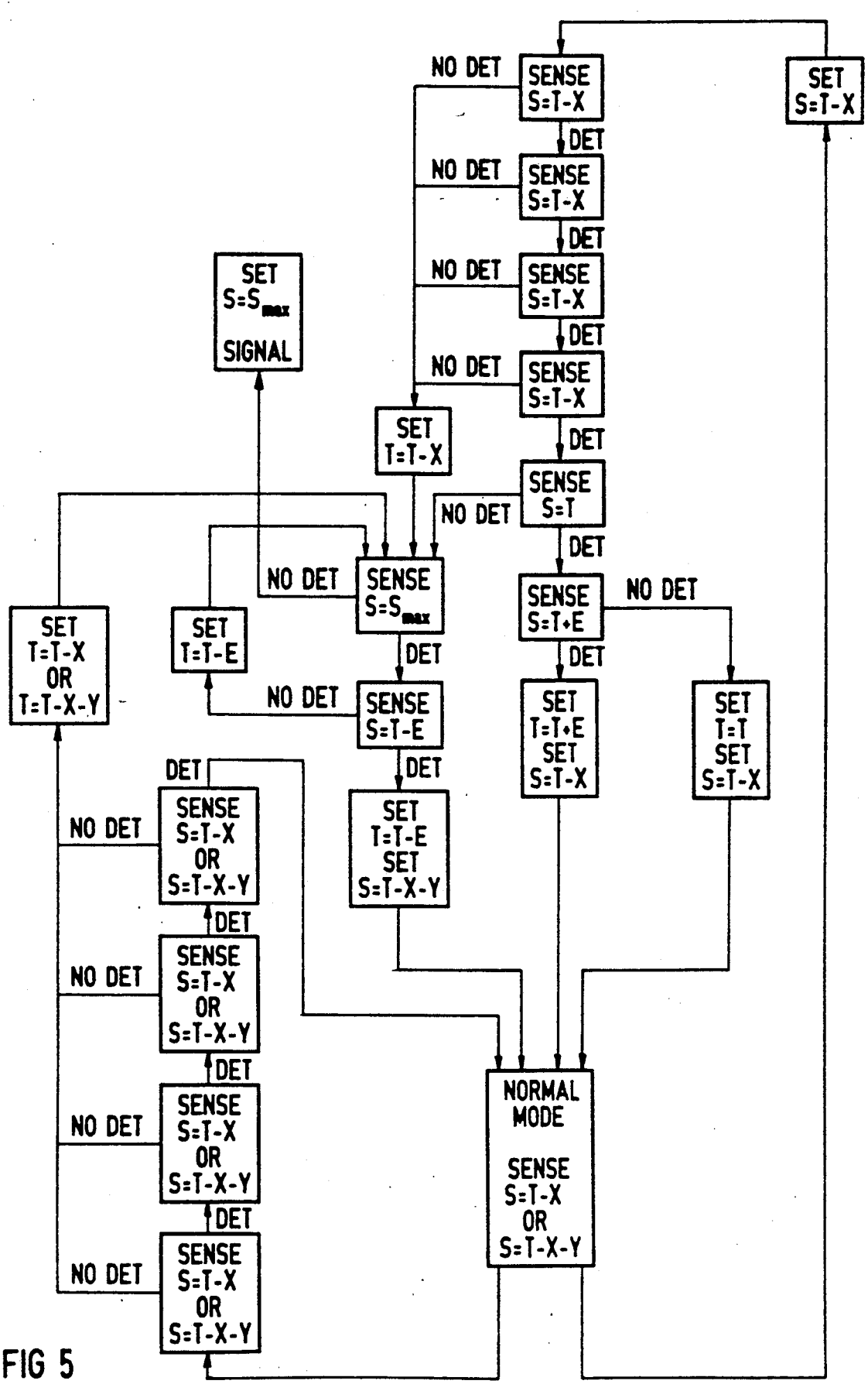
FIG. 5 is a flow chart illustrating a method for automatically adjusting sensitivity of a first detector means of the heart pacemaker of FIG. 1.

The automatic setting of the stimulation intensity and the setting of the sensitivity of the detector means having been set forth, the operating methods with respect thereto shall now be set forth in greater detail in conjunction with FIGS. 4 and 5.

FIG. 4 illustrates an operating method for automatically setting the stimulation intensity, i.e. the energy content of the stimulation pulses. In accordance therewith, a continuous setting of the stimulation intensity does not occur. On the contrary, the heart pacemaker is usually in an operating mode referred to as "NORMAL MODE" wherein the second detector means 43 is switched off and the microprocessor 5 is not activated in any way whatsoever for setting the energy content of the stimulation pulses. This saves energy and makes it possible to change the stimulation intensity without disadvantaging the patient since the stimulation threshold usually changes only very slowly, so that to undertake an automatic setting of the energy content of the stimulation pulses at longer time intervals is adequate.

In the illustrated embodiment, the setting operation occurs between time intervals on the order of hours. During these time intervals, the stimulation pulse generator 20 stimulates the heart with stimulation pulses having an energy content A that was set during the most recently undertaken, automatic setting of the energy content. This energy content A is composed of the minimum energy content V corresponding to the stimulation threshold that is required in order to trigger a stimulated heartbeat detectable with the second detector means 43 and of a safety margin M. In special cases that shall be set forth below, an additional safety margin N that, for example, can amount to 25% of the minimum energy content V can also be present.

The fact that the stimulation pulse generator 20 generates a stimulation pulse with the energy content A in the "NORMAL MODE" is illustrated by the steps (where "STIM" is a command to stimulate) STIM $A=V+M$ and, respectively, STIM $A=V+M+N$. In FIG. 4, moreover, the association of the command STIM with a particular defined energy content A always denotes that a stimulation pulse with the content A is output.

During the course of the automatic setting of the stimulation, the second detector means 43 is activated and a check is carried out for a defined plurality of stimulation pulses having, e.g., the energy content $A=V+M$ to determine whether the second detector means 43 detects a stimulated heartbeat. The detection of a stimulated heartbeat is indicated in FIG. 4 by the flag DET, whereas the absence of detection of a stimulated heartbeat following a stimulation is indicated by the flag NO DET. The energy content A of each of the stimulation pulses thereby amounts to $A=V+M$ regardless of whether the additional safety margin N was previously present.

When a stimulated heartbeat is detected for each of the defined plurality of stimulation pulses, the next stimulation pulse is generated with the minimum energy content V. When this stimulation pulse also leads to the detection of a stimulated heartbeat, a stimulation pulse having an energy content of $A=V-I$, i.e., V diminished by a defined step I, is output as the next stimulation. For example, the step I can be a defined fraction of the maximally possible energy content $A_{max}$ of the stimulation pulses. When this stimulation pulse also leads to the detection of a stimulated heartbeat, this means that the stimulation threshold has dropped. The most recent existing value reduced by the step I is therefore set as the new minimum energy content V and the new minimum energy content V increased by the safety margin M is set as the new energy content A of the stimulation pulses. This is indicated in FIG. 4 by the command SET $V=V-I$ and SET $A=V+M$ (where SET means to set a value). In FIG. 4, moreover, the command SET in combination with the specification of a parameter always denotes that a new value is allocated to this parameter. The heart pacemaker then stimulates in the "NORMAL MODE" with the newly set energy content A that, please note, is lower by the step I than that previously present.

It is conceivable that the stimulation threshold between two successive, setting procedures drops to such an extent that a lowering of the minimum energy content V by more than one step I can occur. In the interest of the safety of the patient, however, lowering the minimum energy content by only one step I is permitted. If the stimulation threshold were in fact to stabilize at a level that allows for further reduction of the energy content A, then the further reduction would still occur early enough during the course of the next regular setting or settings of the energy content A.

When a stimulation pulse having the energy content $A=V-I$ does not lead to the detection of a stimulated heartbeat, this denotes that the stimulation threshold has not changed since the most recent, setting procedure. The earlier minimum energy content V and the earlier energy content A are therefore set again before the return into the "NORMAL MODE" ensues.

When stimulation with the most recently found minimum energy content V does not lead to the detection of a stimulated heartbeat, the stimulation threshold is considered risen. Then a stimulation pulse having the maximally possible energy content $A_{max}$ is first output in order to assure that no more than one stimulation pulse remains unsuccessful.

When, following this stimulation pulse having the maximum energy content $A_{max}$, a stimulated heartbeat is detected, a stimulation with an energy content $A=V+I$ that corresponds to the most recent minimum energy content V increased by a step I ensues. When this leads to the detection of a stimulated heartbeat, the new minimum energy content V is correspondingly set. Differing from before, however, it is not only the sum of the new minimum energy content V and of the safety margin M that is set as new energy content A. On the contrary, a further increase of the energy content A by the afore-mentioned, additional safety margin N ensues. Stimulation with an energy content $A=V+M+N$ is thus carried out in the "NORMAL MODE" until the next setting of the energy content A. This is done in order to undertake appropriate precautions in the interest of the safety of the patient in case of a further increase of the stimulation threshold. In case no further rise of the stimulation threshold occurs before the next, setting procedure, the additional safety margin N is again eliminated, as derived from the explanations above.

When stimulation with the minimum energy content V increased by a step I does not lead to the detection of a natural heartbeat, the minimum energy content V is increased by a further step I. However, a stimulation with the maximum energy content $A_{max}$ ensues first. Only when a stimulated heartbeat is subsequently detected, does stimulation with an energy level equal to the minimum energy V plus an increment I and further increment I occur. This is repeated until a minimum energy content V is found that leads to the detection of a stimulated heartbeat, whereupon the new energy content A is set for the "NORMAL MODE" as set forth immediately above, this being higher than the previously existing energy content A corresponding to the plurality of steps I and by the additional safety margin N.

When a stimulation with the maximum energy content $A_{max}$ also does not lead to the detection of a stimulated heartbeat, the maximum energy content $A_{max}$ is set as the energy content A for all further stimulations and the second detector means 43 is switched off. As indicated by the command SIGNAL, moreover, steps are undertaken so that in the next communication of the programmer 37 with the heart pacemaker 1, a message is output for an attending physician to see that an automatic setting of the energy content A of the stimulation pulses was not possible and a switch was therefore undertaken to the maximum energy content $A_{max}$.

When one of the defined plurality of stimulation pulses that, as set forth, are output at the beginning of a procedure for setting the energy content A of the stimulation pulses already does not lead to the detection of a stimulated heartbeat, this means that the stimulation threshold has risen to such an extent, for example due to a dislocation of the end of the electrode implanted into the heart, that a minimum energy content V of the stimulation pulses is required that is higher than the energy content $A=V+M$. Thus, the minimum energy content V is initially increased to $V=V+M$ before the output of a stimulation pulse with the maximum energy content $A_{max}$ ensues, this being followed by the previously described method steps for calculating a new minimum energy content V and by the fixing of the new energy content A taking the additional safety margin N into consideration before a return into the "NORMAL MODE" ensues.

Between two successive, regular setting procedures, at least one intermediate check to determine whether the detection of a stimulated heartbeat occurs after a defined plurality of stimulation pulses having the most recently set energy content, i.e. $A=V+M$ or $A=V+M+N$, is carried out. If a plurality of such intermediate checks are carried out, they are separated from one another by a time interval having a duration on the order of magnitude of, for example, minutes. To this end, the "NORMAL MODE" is left and the second detector means 43 is activated. When the appearance of a stimulated heartbeat is detected for all stimulation pulses of the defined plurality (four pulses in the case of FIG. 4), a return to the "NORMAL MODE" ensues. When, by contrast, the detection of a stimulated heartbeat is absent for one of the stimulation pulses, a stimulation with the maximum energy content $A_{max}$ ensues next. Thereafter, a new minimum energy content V and a new energy content $A=V+M+N$ of the stimulation pulses is set in the way already set forth and a return into the "NORMAL MODE" is undertaken with this value.

The described checking of a second time ensues in the interest of the safety of the patient in order to be able to quickly do justice to potential disturbances or abnormal changes of the stimulation threshold.

As a comparison of FIGS. 4 and 5 shows, the operating method for automatically adjusting the sensitivity of the first detector means 27 shown in FIG. 5 is similar to the operating method for automatically setting the energy content of the stimulation pulses.

Similarly, a continuous sensitivity setting does not take place with respect to the sensitivity of the first detector means 27. On the contrary, the heart pacemaker is usually in its operating mode referred to as "NORMAL MODE" wherein the second detector means 43 is switched off. This can also be done without disadvantaging the patient in view of the setting of the sensitivity of the first detector means 27 since the conditions usually do not change so quickly that a continuous setting of the sensitivity of the first detector means 27 would be required. It is thus adequate to undertake a setting of the sensitivity between time intervals having a duration on the order of magnitude of hours. The times for automatically setting the sensitivity of the first detector means 27 are expediently selected such that they occur immediately before or immediately after the times during which the automatic setting of the energy content of the stimulation pulses ensues.

During the time intervals laying between successive sensitivity setting procedures, the sensitivity of the first detector means 27 corresponds to the sensitivity set at the most recently undertaken, automatic setting procedure. This sensitivity S is composed of a minimum sensitivity T, that is required so that a natural heartbeat detected with the second detector means 43 is also detected with the first detector means 27, and of a safety margin X of the sensitivity. In special cases that shall be set forth later, an additional safety margin Y of the sensitivity that, for example, can amount to 25% of the minimum sensitivity T can also be present.

The fact that the first detector means 27 is set to the sensitivity S is illustrated by the command SENSE $S=T-X$ or, respectively, SENSE $S=T-X-Y$. The safety margins X or, respectively, Y are thereby subtracted from the minimum sensitivity T since a higher sensitivity S usually corresponds to a lower numerical value of the sensitivity S. In FIG. 5, the association of the command SENSE with the specification of a specific sensitivity S, moreover, always denotes that the sensitivity S of the first detector means 27 is set to the specific sensitivity value.

The second detector means 43 is activated during the course of the automatic setting of the sensitivity S of the first detector means 27. A check is then carried out for a defined plurality of natural heartbeats detected by the second detector means 43, these natural heartbeats preferably being four in number, to see whether these are also detected by the first detector means 27 that is set to the sensitivity $S=T-X$, namely regardless of whether the additional safety margin Y was previously present in the "NORMAL MODE". The detection of a natural heartbeat by the first detector means 27 is illustrated in FIG. 5 by the flag DET. When the first detector means 27 fails to detect a heartbeat detected with the second detector means 43, this is illustrated by the flag NO DET.

When all natural heartbeats of the defined plurality of natural heartbeats detected by the second detector means 43 are also detected by the first detector means 27, the sensitivity S of the first detector means 27 is set to the most recently found minimum sensitivity T. When the first detector means 27 then detects the next natural heartbeat also detected by the second detector means 43, the sensitivity S of the first detector means 27 is again reduced by a defined step E to $S=T+E$. For example, the step E can be a defined fraction or a multiple of the maximally possible sensitivity $S_{max}$ of the first detector means 27. When the first detector means 27 having the sensitivity $S=T+E$ also detects the next natural heartbeat detected by the second detector means 43, $T=T+E$ is set as the new minimum sensitivity T of the first detector means 27 and $S=T-X$ is set as the new sensitivity S of the first detector means 27, this being illustrated by the commands SET $T=T+E$ and SET $S=T-S$. In combination with the specification of a parameter, moreover, the command SET in FIG. 5 always denotes that a new setting of the corresponding parameter to the recited value ensues. The first detector means 27 is then set in the "NORMAL MODE" to the new sensitivity S is lower by the step E than that sensitivity that was previously present.

It is possible that the conditions between two successive, sensitivity setting procedures change so greatly that a reduction of the minimum sensitivity T by more than one step E would be possible. Preferably, in the interest of the safety of the patient, a reduction by only one step E is permitted to be undertaken. Should the conditions in fact stabilize at a level that allows a further reduction of the sensitivity S of the second detector means 27, this then ensues in the course of the next automatic setting or settings of the sensitivity S.

When the first detector means 27 having the sensitivity $S=T+E$ does not detect the next natural heartbeat detected by the second detector means 43, this means that the conditions have not changed since the most recent sensitivity setting procedure. The minimum sensitivity T and the sensitivity S are therefore reset to the previously existing values before a return into the "NORMAL MODE" ensues.

When the first detector means 27 fails to detect a natural heartbeat detected by the second detector means 43 given the most recent existing minimum sensitivity T, this means that an increase in the minimum sensitivity T must ensue. In order to maintain the proper function of the heart pacemaker 1 to the farthest possible degree in the interests of the patient, the sensitivity S, however, is initially set to its maximum value $S_{max}$ until the detection of the next natural heartbeat, this maximum value $S_{max}$, however, being selected such that disturbances and muscle tics cannot lead to misdetections. When the next natural heartbeat detected with the second detector means 43 is also detected by the first detector means 27 set to the maximum sensitivity $S_{max}$, the first detector means 27 is set to a sensitivity S that corresponds to the most recently present minimum sensitivity T increased by the step E. When the first detector means 27 having this sensitivity S detects the next natural heartbeat detected by the second detector means 43, the new minimum sensitivity T is correspondingly fixed. In contrast to previous settings, however, it is not the minimum sensitivity T increased by the safety margin X that is set as new sensitivity S. On the contrary, a further increase by the afore-mentioned additional safety margin Y ensues. In the "NORMAL MODE", the sensitivity of the first detector means 27 is thus set to $S = T - X - Y$ until the next sensitivity setting procedure. This is done in order to undertake precautionary measures in the interests of the safety of the patient that already correspond to the case wherein a further increase in the minimum sensitivity T were to become needed. It is understood from the above explanations that the additional safety margin Y is in turn eliminated when no further increase in the minimum sensitivity T is required up to the next sensitivity setting procedure.

When the minimum sensitivity T of the first detector means 27 increased by a step E is not adequate for detection of a natural heartbeat by the second detector means 43, the minimum sensitivity T is increased by a further step E. First, however, the sensitivity of the first detector means 27 is set to its maximum value $S_{max}$ in order to enable the detection of the next natural heartbeat. Only when this detection has occurred is a check carried out for the subsequent natural heartbeat detected by the second detector means 43 to determine whether detection also occurs with the first detector means 27 having its sensitivity S increased by a further step E. This is repeated until a new minimum sensitivity T is found with which the first detector means 27 also detects a natural heartbeat detected by the second detector means 43. Thereafter, the new minimum sensitivity T and the new sensitivity S are set as set forth immediately above and a switch into "NORMAL MODE" is undertaken with these values, whereby the safety margin X and the additional safety margin Y are then present.

When a natural heartbeat detected by the second detector means 43 is not detected by the first detector means 27, even when the first detector means 27 is set to its maximum sensitivity $S_{max}$, the sensitivity S of the first detector means 27 is thus set to its maximum value $S_{max}$ for the further operation of the heart pacemaker. Steps are also undertaken to assure that the attending physician is informed at the next communication of the programmer 37 with the heart pacemaker 1 that the sensitivity of the first detector means 27 was set to its maximum value $S_{max}$. Alternatively, instead of setting the sensitivity of the first detector means to its maximum value $S_{max}$, it can also be provided that the first detector means 27 is deactivated and is replaced by the second detector means 43.

When the first detector means 27 has its sensitivity S set to the value $S = T - X$ but does not detect one of the plurality four (in the illustrated embodiment) of natural heartbeats detected with the second detector means 43 at the beginning of the described operating method, this means that the minimum sensitivity T of the first detector means 27 must be increased by more than the safety margin X in order to enable for the first detector means 27 to detect a natural heartbeat detected by the second detector means 43. In this case, a new minimum sensitivity T is first set, new minimum sensitivity T corresponding to the previously sensitivity S. Thereafter, the above-described procedure is carried out in order to calculate the minimum sensitivity T, whereupon a return to the "NORMAL MODE" ensues after the setting of a corresponding sensitivity S.

In a manner similar to the automatic setting of the energy content A of the stimulation pulses, an intermediate check to determine whether the setting of the sensitivity S present in the "NORMAL MODE" is essentially still correct is carried out between two successive, sensitivity setting procedures for the first detector means 27. If a plurality of intermediate checks are made, the time intervals therebetween are relatively short, i.e., they have a duration on the order of magnitude of minutes. To this end, the "NORMAL MODE" is left and the second detector means 43 is activated. For a defined plurality of natural heartbeats detected by the second detector means 43 (these natural heartbeats are four in number in the illustrated embodiment of FIG. 5), a check is then carried out to determine whether these heartbeats are also detected by the first detector means 27. When this is the case for all natural heartbeats of the defined plurality, a return to the "NORMAL MODE" ensues. When the first detector means 27 fails to detect one of the natural heartbeats, the minimum sensitivity T is reset to a value that corresponds to the sensitivity S previously present in "NORMAL MODE". The calculation of a new minimum sensitivity T in the way set forth above follows thereupon, and this is followed by a return to the "NORMAL MODE" after the determination and setting of a new sensitivity S for the first detector means 27.

The times for the setting procedures and intermediate checks are expediently calculated by the microprocessor 5 in that it counts a corresponding plurality of clock pulses generated by the crystal 14.

Critical functions of the heart pacemaker of the described exemplary embodiment are controlled by a suitably programmed microprocessor 5. The corresponding functions, however, can also be realized without a traditionally constructed control logic.

Insofar as an automatic setting of the sensitivity of the detector means serving the purpose of detecting natural heartbeats is not desired, the entire channel 15 including the first detector means 27 can be eliminated. The function thereof is then assumed by the second detector means 43. Differing from the described exemplary embodiment, natural heartbeats are only detected by the detector means 43. Consequently, the inhibition of the output of stimulation pulses ensues on the basis of the output signals of the detector means 43, in the manner set forth above in conjunction with the detector means 27.

Although the invention has been set forth only with reference to a heart pacemaker, it can also be employed in other medical devices that comprise a detector means having variable sensitivity.

While a preferred embodiment has been shown, modifications and changes may become apparent to those skilled in the art which shall fall within the spirit and scope of the invention. It is intended that such modifications and changes be covered by the attached claims.

I claim as my invention:

1. A medical device implantable into the body of a living being comprising first detector means for detecting events relating to a physiological function of the living being; setting means for setting the sensitivity (S) of the first detector means; and second detector means for detecting the events relating to the physiological function, the sensitivity thereof at least corresponding to the sensitivity (S) of the first detector means, and wherein the setting means is connected to the second detector means automatically sets the sensitivity (S) of the first detector means such that the first detector means detects each event detected by the second detector means.

2. The device of claim 1, wherein the setting means comprises means for setting the sensitivity (S) of the first detector means to a value that is higher by a safety margin (M) than a minimum value (T) at which the first detector means detects every event detected by the second detector means.

3. The device of claim 2, wherein, for calculating the minimum value (T), the setting means comprises means for gradually increasing the sensitivity (S) of the first detector means from a value at which the first detector means does not detect any event detected by the second detector means, to a value at which the first detector means just detects every event detected by the second detector means; and wherein, for calculating that value of the sensitivity (S) of the first detector means at which said first detector means does not detect any events detected by the second detector means, the setting means further comprising means for gradually reducing the sensitivity (S) of the first detector means from a value at which the first detector means detects every event detected by the second detector means until a value at which the first detector means no longer detects any events detected by the second detector means.

4. The device of claim 1, wherein the device is a heart pacemaker whose first and second detector means are provided for detecting natural heartbeats.

5. The device of claim 4, wherein the first detector means comprises means for natural heartbeats in a signal corresponding to the electrical activity of the heart and the second detector means comprises means for detecting natural heartbeats in a signal (IS) corresponding to a chronological curve of the electrical impedance of the heart.

6. The device of claim 1, wherein the second detector means comprises a modulatable current source; a demodulator circuit; an oscillator circuit that generates a periodic oscillator signal (P) and is connected to the current source and to the demodulator circuit; and a detector circuit, whereby the oscillator signal (P) modulates the current source such that said current source outputs an alternating current (Q) having a constant amplitude that is synchronized with the oscillator signal (P), an alternating voltage component (R) of the voltage dropping off across the current source being supplied to the demodulator circuit that is synchronized with the current source in response to the oscillator signal (P) and that demodulates the alternating voltage component (R), and a demodulated signal (U) being supplied to the detector circuit.

7. The device of claim 6, wherein the current source of the second detector means comprises two terminals to which a bipolar electrode is connectible.

8. A method for the operation of an implantable medical device implantable into the body of a living being comprising a first detector means for the detection of events occurring with respect to a physiological function of the living being; setting the sensitivity (S) of the first detector means; and a second detector means for the detection of the events occurring with respect to the physiological function, setting the sensitivity thereof at least corresponding to the respectively set sensitivity (S) of the first detector means, setting the sensitivity (S) of the first detector means such that the first detector means detects the events detected by the second detector means, and further comprising the step of automatically setting the sensitivity (S) of the first detector means between successive regular intervals.

9. The method of claim 8, comprising the further step of determining, at least once between automatic settings of the sensitivity of the first detector means, whether an event detected by said second detector means is also detected by said first detector means.

10. The method of claim 9 wherein, when an event detected by the second detector means is not detected by the first detector means using the most recently set sensitivity value (S) as the minimum sensitivity value (T) in the automatic setting of the sensitivity (S) of the first detector means.

11. The method of claim 9 further comprising setting the sensitivity (S) of the first detector means to a maximum value ($S_{max}$) for the detection of the next event when an event detected by the second detector means is not also detected by the first detector means.

12. The method of claim 9, comprising the further step of calculating and storing a minimum sensitivity value (T) at which the first detector means just detects energy events detected by the second detector means during an automatic setting of the sensitivity (S) of the first detector means.

13. The method of claim 12, wherein the first detector means does not detect every event detected by the second detector means, the step of calculating a minimum sensitivity value (T) comprises the steps of increasing the sensitivity (S) of the first detector means by defined increments (E) until the first detector means detects a defined plurality of events detected by the second detector means.

14. The method of claim 12, wherein the step of calculating the minimum sensitivity value (T) comprises:

setting the sensitivity (S) of the first detector means equal to the previous minimum sensitivity value (T);

determining if the first and second detector means detect the same plurality of events;

if the first and second detector means detect the same plurality of events, setting the minimum sensitivity value (T) equal to the previous minimum sensitivity value (T) less an increment (E);

if the first and second detector means do not detect the same plurality of events, setting the minimum sensitivity value (T) equal to the previous minimum sensitivity value (T).

15. The method of claim 12, comprising the further step of determining whether an event is detected by both the first and second detector means with the sensitivity (S) of the first detector means reduced by the additional safety margin (4) prior to calculation of the minimum sensitivity value (T); and if the event is not detected by both the first and second detector means, setting the minimum sensitivity value (T) equal to the sensitivity value (S).

16. The method of claim 12, comprising the further step of setting the sensitivity (S) of the first detector means to a sensitivity that is equal to the minimum sensitivity (T) plus a safety margin (X).

17. The method of claim 16, comprising the step of setting the sensitivity (S) to be equal to the previously set sensitivity (S) of the first detector means plus an additional safety margin (4) whenever the most recently calculated minimum sensitivity value (T) is greater than the previously calculated minimum sensitivity value (T).

18. The method of claim 16, comprising the step of setting the sensitivity (S) of the first detector means equal to the previously set sensitivity less an additional safety margin (4) whenever the most recently calculated minimum sensitivity value (T) is less than or equal to the previously calculated minimum sensitivity value (T).

* * * * *